(12) United States Patent
Sward

(10) Patent No.: US 11,865,233 B2
(45) Date of Patent: Jan. 9, 2024

(54) AIR TREATMENT APPLIANCE

(71) Applicant: Prolitec Inc., Seattle, WA (US)

(72) Inventor: Nathan Sward, Wauwatosa, WI (US)

(73) Assignee: Prolitec Inc., Seattle, WA (US)

( * ) Notice: Subject to any disclaimer, the term of this patent is extended or adjusted under 35 U.S.C. 154(b) by 0 days.

(21) Appl. No.: 17/486,788

(22) Filed: Sep. 27, 2021

(65) Prior Publication Data

US 2023/0096168 A1 Mar. 30, 2023

Related U.S. Application Data

(60) Provisional application No. 63/248,515, filed on Sep. 26, 2021.

(51) Int. Cl.
*A61L 9/14* (2006.01)

(52) U.S. Cl.
CPC ............ *A61L 9/14* (2013.01); *A61L 2209/111* (2013.01); *A61L 2209/12* (2013.01); *A61L 2209/133* (2013.01); *A61L 2209/134* (2013.01); *A61L 2209/15* (2013.01)

(58) Field of Classification Search
CPC .. A61L 9/14; A61L 2209/111; A61L 2209/12; A61L 2209/133; A61L 2209/134; A61L 2209/15
See application file for complete search history.

(56) References Cited

U.S. PATENT DOCUMENTS

| | | | |
|---|---|---|---|
| 5,533,497 A | 7/1996 | Ryder | |
| 6,478,440 B1 | 11/2002 | Jaworski et al. | |
| 6,779,905 B1 * | 8/2004 | Mazursky | F21V 1/10 362/86 |
| 6,950,607 B2 | 9/2005 | Yip et al. | |
| 7,503,668 B2 | 3/2009 | Porchia et al. | |

(Continued)

FOREIGN PATENT DOCUMENTS

| | | |
|---|---|---|
| EP | 2 433 656 A1 | 3/2012 |
| JP | 2020103678 A | 7/2020 |
| WO | WO 2018/026932 A1 | 2/2018 |

OTHER PUBLICATIONS

Invitation to Pay Additional Fees, dated Dec. 16, 2022, for International Patent Application No. PCT/US2022/042885. (12 pages).

(Continued)

*Primary Examiner* — Regina M Yoo
(74) *Attorney, Agent, or Firm* — SEED IP LAW GROUP LLP

(57) ABSTRACT

An air treatment system is provided which includes an appliance and a replaceable cartridge installable therein. The replaceable cartridge contains a liquid compound to be aerosolized and has a cartridge outlet through which the aerosolized compound is discharged during operation. A pump is provided to supply air to the replaceable cartridge to generate the aerosolized compound from the liquid compound contained in the replaceable cartridge, and a controller is provided for controlling the pump to supply the air to the replaceable cartridge to generate and discharge the aerosolized compound from the appliance. The appliance is particularly adapted to be plugged into an electrical wall outlet to be supported by the same within a room for treating the interior air space thereof.

24 Claims, 6 Drawing Sheets

(56) References Cited

U.S. PATENT DOCUMENTS

| | | | |
|---|---|---|---|
| 7,712,683 B2 | 5/2010 | Robert et al. | |
| 7,840,123 B2 * | 11/2010 | Belongia | A01M 1/2072 |
| | | | 392/392 |
| 7,930,068 B2 | 4/2011 | Robert et al. | |
| 7,932,482 B2 | 4/2011 | Norwood et al. | |
| 8,061,562 B2 * | 11/2011 | Carpenter | B05B 12/12 |
| | | | 239/70 |
| 8,590,743 B2 * | 11/2013 | Beland | B65D 83/46 |
| | | | 222/1 |
| 8,740,015 B2 * | 6/2014 | McLisky | B65D 83/262 |
| | | | 222/52 |
| 8,855,827 B2 | 10/2014 | Weening et al. | |
| 9,162,004 B1 | 10/2015 | Ansley et al. | |
| 9,205,166 B2 * | 12/2015 | Segura Rius | A61L 9/015 |
| 9,248,461 B2 * | 2/2016 | Ansley | B05B 7/2489 |
| 9,358,562 B2 | 6/2016 | Ansley et al. | |
| 9,439,995 B2 | 9/2016 | Conroy et al. | |
| 9,527,094 B1 * | 12/2016 | Levy | B05B 14/00 |
| 9,746,371 B1 * | 8/2017 | Kumar | H05B 45/12 |
| 10,973,944 B1 * | 4/2021 | Farrell | A61L 9/14 |
| 2002/0130146 A1 | 9/2002 | Borut et al. | |
| 2004/0074935 A1 * | 4/2004 | Chon | A61L 9/14 |
| | | | 222/646 |
| 2005/0220664 A1 | 10/2005 | Hitzler et al. | |
| 2006/0237439 A1 * | 10/2006 | Norwood | A01M 1/2077 |
| | | | 219/506 |
| 2010/0326280 A1 * | 12/2010 | Hicks | A61L 9/048 |
| | | | 96/222 |
| 2011/0132995 A1 * | 6/2011 | Perman | A61L 9/03 |
| | | | 239/34 |
| 2012/0205462 A1 | 8/2012 | Burke et al. | |
| 2013/0026250 A1 | 1/2013 | Burt et al. | |
| 2013/0068786 A1 | 3/2013 | Gasper et al. | |
| 2013/0079733 A1 | 3/2013 | Burt et al. | |
| 2014/0079597 A1 | 3/2014 | Segura Rius et al. | |
| 2014/0091487 A1 | 4/2014 | Belongia | |
| 2014/0212334 A1 | 7/2014 | Klein et al. | |
| 2015/0019029 A1 | 1/2015 | Chandler et al. | |
| 2015/0297776 A1 | 10/2015 | Conroy et al. | |
| 2015/0367014 A1 | 12/2015 | Gruenbacher et al. | |
| 2015/0368001 A1 | 12/2015 | Gruenbacher et al. | |
| 2016/0175474 A1 * | 6/2016 | Ansley | A61M 11/02 |
| | | | 261/74 |
| 2016/0339135 A1 * | 11/2016 | Becker | G08B 21/182 |
| 2018/0100498 A1 * | 4/2018 | Ansley | B05B 7/2489 |
| 2018/0290156 A1 * | 10/2018 | Gruenbacher | B05B 17/0684 |
| 2018/0290157 A1 * | 10/2018 | Gruenbacher | B41J 2/1752 |
| 2018/0290158 A1 * | 10/2018 | Gruenbacher | B05B 7/0815 |
| 2018/0290159 A1 * | 10/2018 | Gruenbacher | B05B 1/24 |
| 2019/0216967 A1 * | 7/2019 | Turner | A61L 9/035 |
| 2019/0275188 A1 | 9/2019 | Hsiao | |
| 2020/0390927 A1 * | 12/2020 | Fischer | A61L 9/037 |
| 2021/0015955 A1 * | 1/2021 | Harrell | A61L 9/03 |
| 2021/0228760 A1 * | 7/2021 | Farrell | A61L 9/127 |

OTHER PUBLICATIONS

International Search Report and Written Opinion in International Application No. PCT/US2022/042885, dated Mar. 22, 2023, 20 pages.

* cited by examiner

AIR TREATMENT APPLIANCE

BACKGROUND

Technical Field

The present disclosure relates generally to air treatment appliances and, more specifically, to air treatment appliances including a replaceable cartridge containing a liquid compound to be diffused or aerosolized and released into a space to be treated. The air treatment appliances are particularly well suited to be plugged into an electrical wall outlet to be supported by the same within a room for treating the interior air space thereof.

Description of the Related Art

Air treatment appliances in the past have had the ability to dispense scent compounds or other compounds throughout the atmosphere of desired spaces but can suffer from various drawbacks or deficiencies. For example, some air treatment appliances and replaceable cartridges thereof may be overly complex, costly and/or suffer from other deficiencies or drawbacks, such as, for example, discharging diffused or aerosolized matter with less than ideal characteristics, or the cartridges being susceptible to leakage, tampering, fouling and/or contamination. Such air treatment appliances include so called plug-in diffusers that typically operate by heating a scented oil compound using electrical energy from an electrical wall socket to which the diffusers are secured to heat the scented oil compound.

BRIEF SUMMARY

The air treatment appliances and replaceable cartridges and other components thereof and related methods shown and described herein provide form factors that are robust, efficient, and particularly effective at treating spaces with a diffused or aerosolized compound from a liquid source, and include air treatment appliances that are specifically configured to be plugged into an electrical wall outlet to be supported by the same within a room for treating the interior air space thereof.

DETAILED DESCRIPTION

In the following description, certain specific details are set forth in order to provide a thorough understanding of various disclosed embodiments. However, one skilled in the relevant art will recognize that embodiments may be practiced without one or more of these specific details. In other instances, well-known devices, structures and techniques associated with air treatment appliances (also referred to as liquid diffusion devices), components thereof and related methods of diffusing or aerosolizing a compound from a liquid source may not be shown or described in detail to avoid unnecessarily obscuring descriptions of the embodiments. For example, embodiments of the air treatment appliances and replaceable cartridges disclosed herein may include or incorporate aspects or features of known appliances and associated components and control methods thereof. Examples of known air treatment appliances, components and aspects thereof and related methods are shown and described in U.S. Pat. Nos. 7,712,683; 7,930,068; 8,855,827; 9,248,461; 9,162,004; and 10,086,340, all of which are incorporated herein by reference in their entirety.

Unless the context requires otherwise, throughout the specification and claims which follow, the word "comprise" and variations thereof, such as "comprises" and "comprising," are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Figure 1:
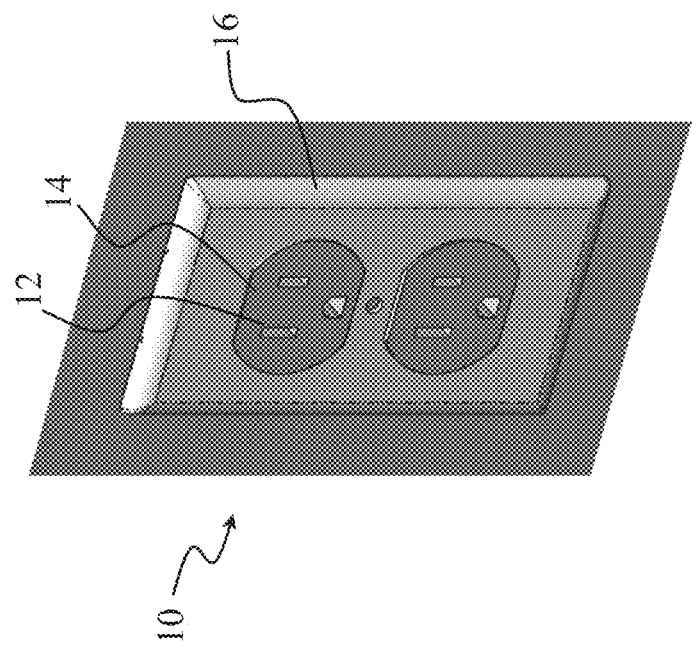
FIG. 1 is a perspective view of an air treatment system, according to one embodiment, including a "plug-in" air treatment appliance for plugging into an electrical wall outlet for treating a space (e.g., an interior of a room of a residential home) with a scent compound or other compound diffused or aerosolized from a liquid contained in replaceable cartridges that may be loaded in the appliance.
Figure 1:
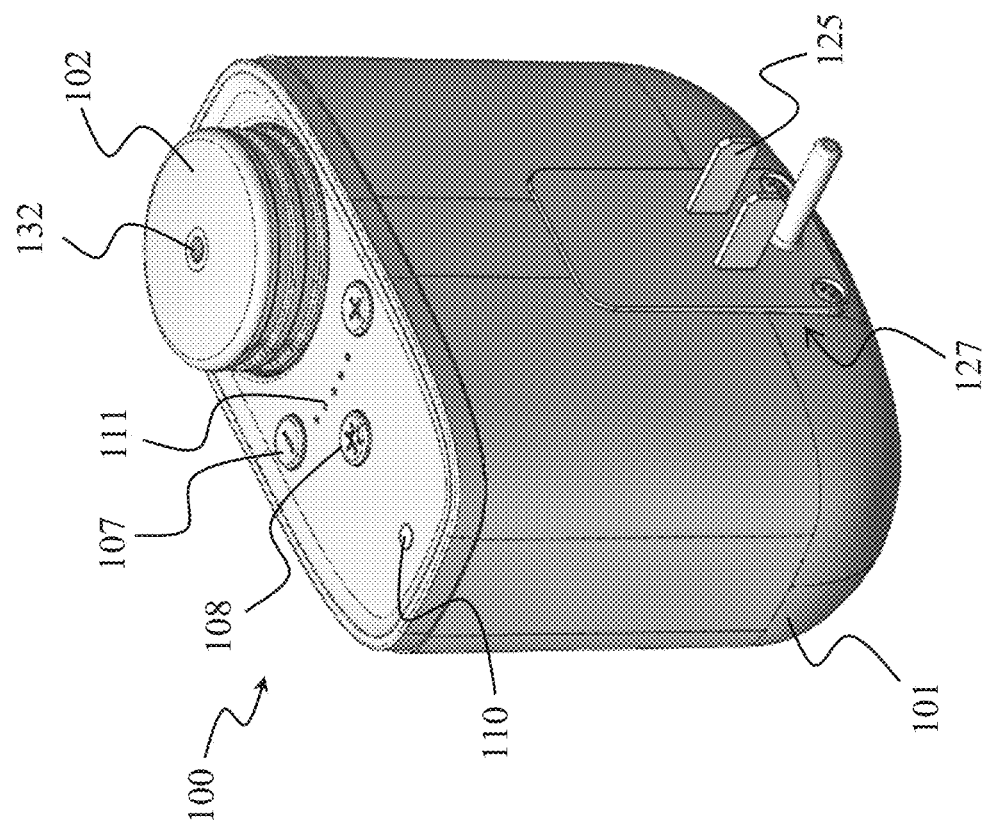

With reference to FIG. 1, the present disclosure relates generally to air treatment appliances 100 and more specifically to air treatment appliances 100 operable with replaceable cartridges 102 containing a liquid compound 120 (FIG. 5) to be diffused or aerosolized and released into a space to be treated, which may also referred to as liquid diffusion devices or apparatuses, and to components thereof and related methods.

As shown in FIG. 1, the air treatment appliances 100 of the present disclosure may be provided in a form factor that is configured to be plugged into an electrical wall outlet 10 and to be supported by the same within a room for treating the interior air space thereof with a scent compound or other compound diffused or aerosolized from a liquid source. In particular, the appliances 100 may include a form factor that is configured to be readily inserted into contact openings 12 of a receptacle 14 of the electrical wall outlet 10 to be supported in a cantilevered manner from the electrical wall outlet 10 for use. Advantageously, the form factor may be relatively compact and may have an overall major dimension that does not exceed, for example, the height of a conventional electrical wall outlet cover plate 16, or 125 percent of the height of a conventional electrical wall outlet cover plate 16.

With continued reference to FIG. 1, each replaceable cartridges 102 includes a cartridge outlet 132 to permit a diffused or aerosolized compound generated from the liquid 120 within the cartridge 102 to be discharged into the environment or space surrounding the appliance 100. More particularly, when loaded, the replaceable cartridge 102 within the appliance 100 is coupled to an outlet of a source of pressurized air (e.g., pump 122 of FIG. 4) to enable pressurized air to be selectively passed through the cartridge 102 as described herein to diffuse or aerosolize the liquid 120 contained therein and to force the aerosolized matter to be discharged through the cartridge outlet 132.

Within the present disclosure, the terms atomize and diffuse may be used in their various forms interchangeably. They are intended to refer to generally the same action, that being the dispersion of liquid into very small particle sizes (preferably but not limited to one micron or less in size) and releasing the particles into the atmosphere of a generally enclosed space. Discharging diffused liquid with particularly small particles helps ensure that the liquid to be dispersed remains airborne long enough to effectively treat the space. The diffused liquid is also referred to herein as aerosolized matter, and may include, for example, a scented compound.

One approach to providing small particle sizes is to incorporate a dispersion or gas-liquid mixing location adjacent an expansion chamber. The mixed gas and liquid combination may contain particles of greater than desirable size. Allowing this mix to remain resident within the expansion chamber prior to release into the treated space will allow larger particles to precipitate out of the mixture. Structures that the gas and liquid mixture impinge upon may also assist in the collection of these larger particles and leave only the desired predominantly smaller sized particles to be released. The expansion chamber may be maintained at a positive pressure with respect to the atmospheric pressure within the space to be treated, so that the gas and liquid mix will be ejected from the appliance 100 into the space. Alternatively, the expansion chamber may generally be maintained at the atmospheric pressure of the space to be treated with the flow of gas (e.g., air) through the chamber providing the impetus for movement of the gas and liquid mix from the cartridge 102 of the appliance 100 into the space to be treated.

Within the context of this disclosure, diffusion or aerosolizing also generally refers to a process or method of dispersing a liquid without destroying the integrity of the liquid compound. While some degree of reactivity between the gas (e.g., air) and the liquid may be desirable, diffusion generally does not change the nature of the liquid, unlike heating or the application of electrical energy into the liquid to diffuse the liquid.

The air treatment appliances 100, replaceable cartridges 102 and other components and methods described herein may be used to provide or introduce a pleasant or soothing scent (or some other type of liquid that may be used as an airborne treatment or compound) into the air space of a room or other generally enclosed space. The particular liquid 120 to be dispensed by the diffusion device is contained within the replaceable cartridge 102. Other possible types of liquids that may be dispersed may include decontamination agents and many different types of liquids that may be desirably dispersed within an enclosed space. The present disclosure is not limited to a particular type or nature of liquid 120 to be dispersed, but is intended to encompass any desirable airborne liquid treatments that are preferably dispersed within an enclosed space to be effective. The term enclosed space, as used herein, refers to any volume of space within which the atmospheric turnover is sufficiently slow to permit the dispersed liquid to have its desired effect within the space. Some spaces may have one or more openings and still have the desired characteristics to permit treatment with a diffused liquid. Other spaces may be preferably fully enclosed to permit treatment by the selected liquid. In other cases, the liquid used for treatment may preferably be used in a sealed space, for maximum effectiveness or for safety reasons. Within the scope of the present disclosure, it is not intended to limit the nature, size or configuration of the space to be treated except as may be appropriate for the liquid used to treat the space and the nature of treatment desired within the space. That said, embodiments described herein are particularly well suited for treating the interior space of a room of a building (e.g., a room of a residential home), which may be fully enclosed or in some instances have one or more openings such as one or more open windows or doors.

Figure 4:
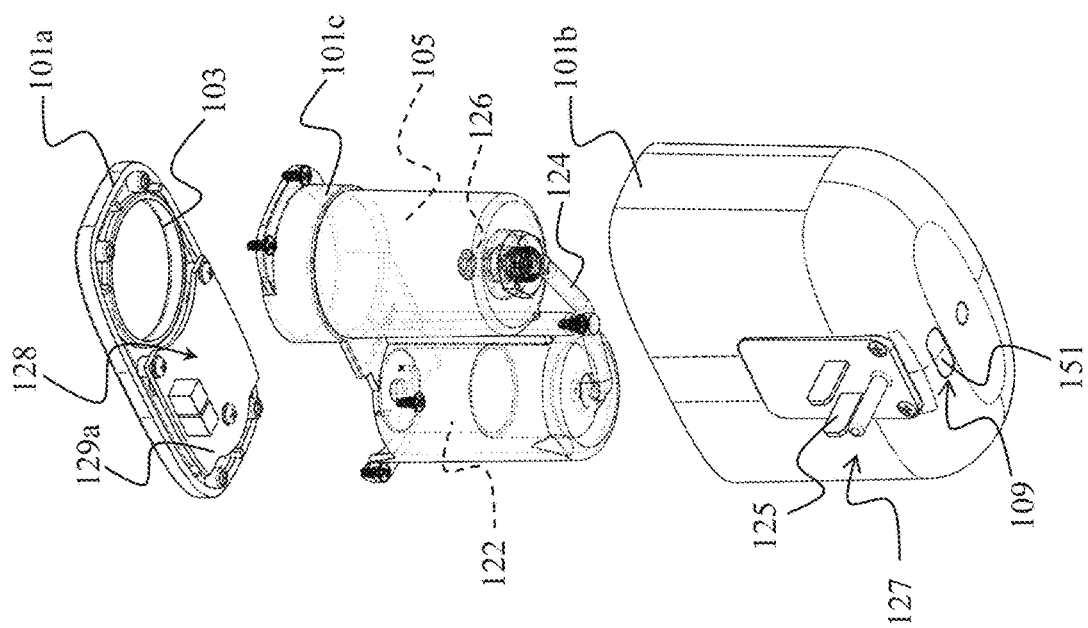
FIG. 4 is a perspective exploded view of the air treatment appliance of FIG. 1.

With reference to FIG. 4, and according to the illustrated embodiment, a control system 128 (inclusive of one or more printed circuit boards, PCBs, 129a, 129b) is provided and is configured to permit adjustment of the timing, flow rate and/or pressure level of the pressurized air generated by a pump assembly 122 that is directed into and passes through an installed cartridge 102 during use, and to provide other functionality described herein. In some instances, the operating pressure may be relatively low, such as, for example, less than about 2 psi gauge pressure or about 1.5 psi gauge pressure. Within the cartridge 102, the pressurized air is directed to atomize the liquid 120 contained therein and to aid in the dispersion of the atomized liquid into the air space to be treated.

In some instances, it may be desirable to have an indirect route from the point of actual atomization of the liquid and a cartridge outlet 132 through which atomized particles exit from the cartridge 102. As will be described in greater detail elsewhere, embodiments of the replaceable cartridges 102 described herein provide an atomization zone where liquid 120 from the cartridge 102 and pressurized air meet and are mixed. In addition, the cartridges 102 may also provide an expansion chamber or chambers within the cartridge 102 where the atomized liquid is retained until a portion of the atomized liquid is allowed to exit the cartridge 102 loaded in the host appliance 100. As described in greater detail elsewhere, the cartridges 102 may combine storage of the liquid 120 to be diffused, an atomization structure to transform the liquid 120 into an airborne concentration, an expansion chamber or chambers, and optionally a tortuous path or passage towards the outlet 132 of the cartridge 102.

With reference to FIGS. 1 through 4, one example embodiment of an air treatment appliance 100 is illustrated and includes an appliance housing 101 configured to receive the cartridges 102 therein. As previously discussed, the appliance 100 is configured to treat a space with a diffused or aerosolized compound generated by a flow of air moving through the cartridge 102 which is entrained with liquid particles from liquid 120 contained in the cartridge 102. For this purpose, the appliance 100 may include one or more controls, such as, for example, user manipulable switches or buttons 107, which may act as a power on/off control for powering up and powering down the appliance 100, as well as an intensity control for adjusting the intensity or quantity of discharged matter into the surrounding environment. The appliance 100 may include another user manipulable switch or button 108, which may act as a on/off control for turning on an off a lighting arrangement 109 (FIGS. 3 and 4) of the appliance 100, and/or act as an intensity control for adjusting the intensity or other characteristics (e.g., color) of the light emitted into the surrounding environment from the appliance 100. The one or more controls may also provide a user interface for calibrating the appliance 100 to recognize light and dark environments to provide additional functionality described herein. The appliance 100 may further include a photodetector 110 mounted to the housing 101, wherein the plug-in liquid diffusion appliance 100 is configured to be controlled using signals generated by the photodetector 110, as described in more detail elsewhere herein. The lighting arrangement 109 may also be controlled using signals generated by the photodetector 110, such as by controlling the lighting arrangement 109 to illuminate when the photodetector 110 senses the surrounding environment is dark, or by controlling the lighting arrangement 109 to turn off when the photodetector 110 senses the surrounding environment is light. In some instances, the photodetector 110 may be mounted to a top of the housing 101 or other upward-facing portion of the housing 101, but it is also contemplated that the photodetector 110 may be located in other locations, e.g., a side or a bottom of the appliance 100) as desired. The appliance 100 may further include one or more indicators 111 (e.g., LEDs) for providing operational feedback signals, such as, for example, an intensity level at which the appliance 100 is operating.

Figure 3:
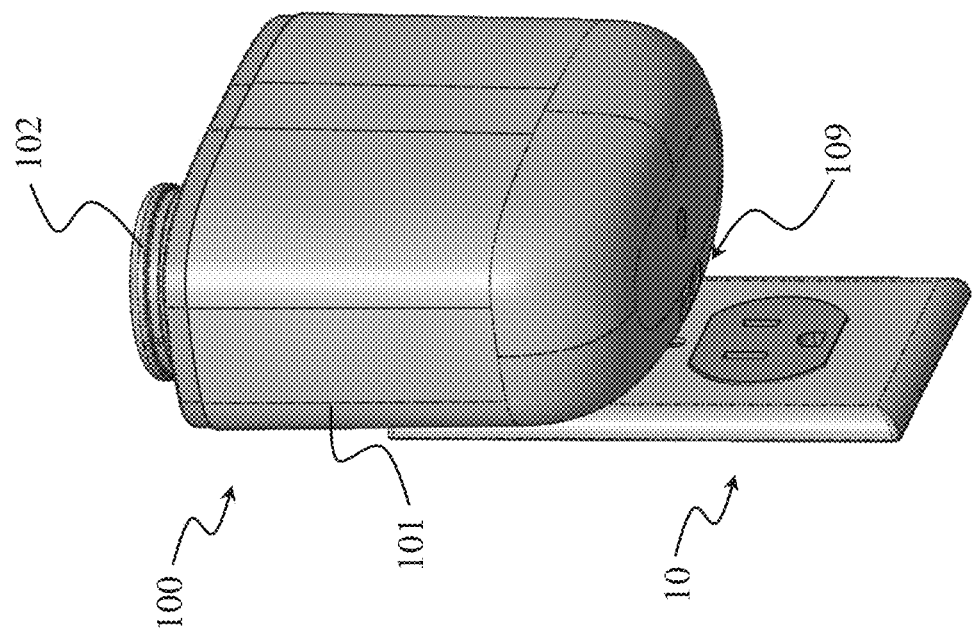
FIG. 3 is a bottom perspective view of the air treatment appliance of FIG. 1 installed in the electrical wall outlet for use.
Figure 2:
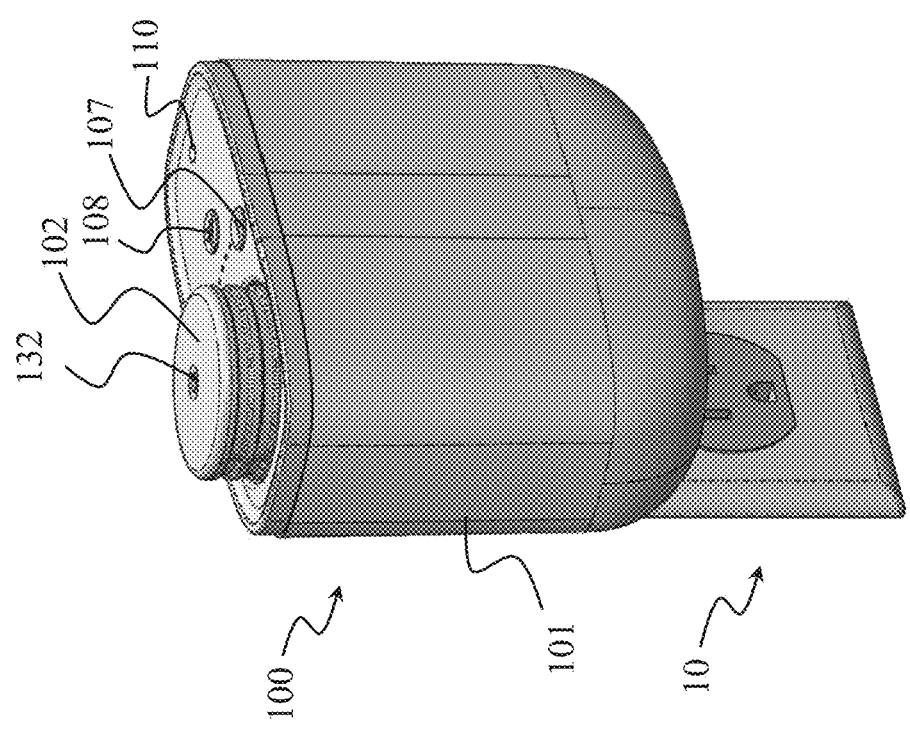
FIG. 2 is a top perspective view of the air treatment appliance of FIG. 1 installed in the electrical wall outlet for use.
Figure 8:
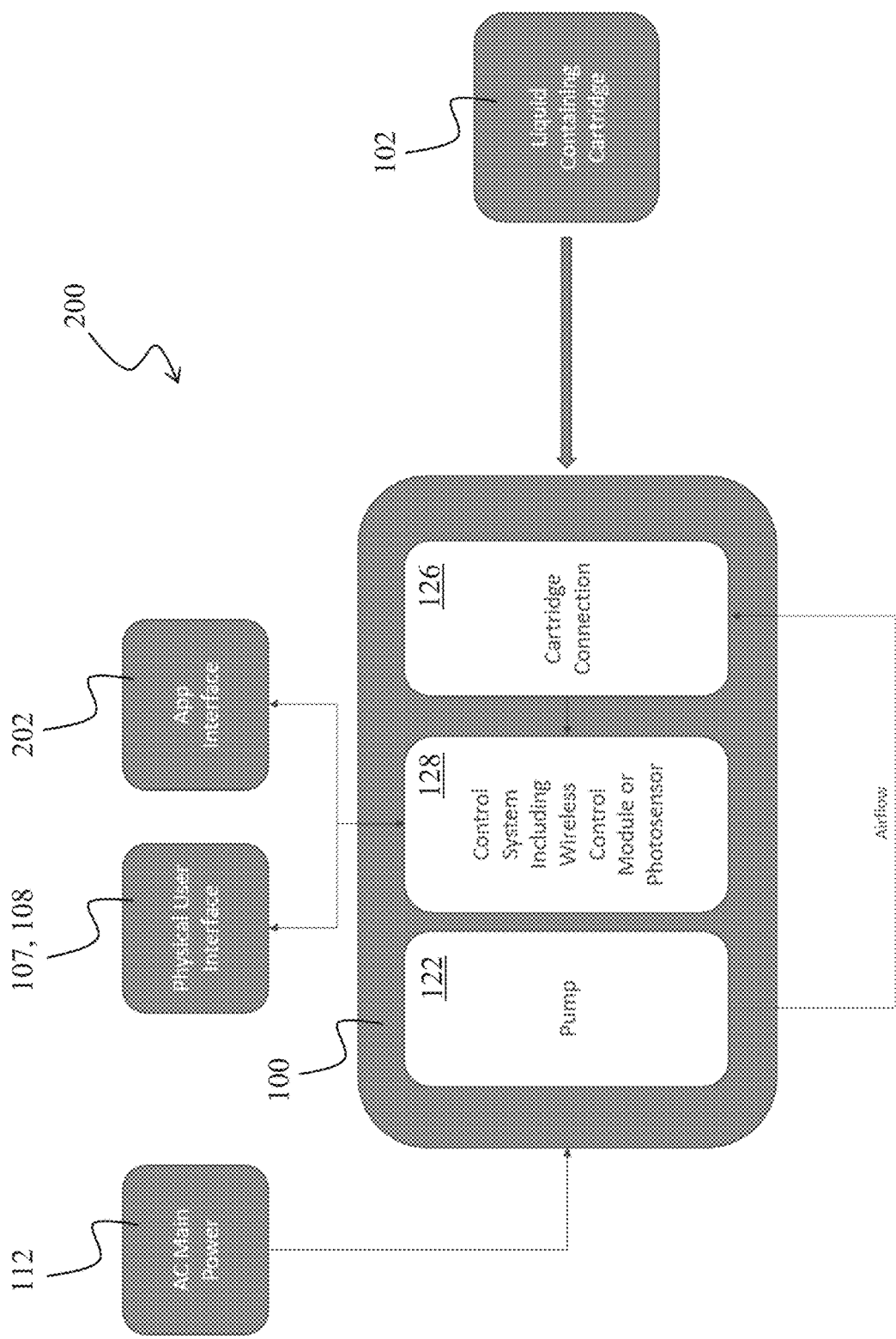
FIG. 8 is a system diagram, according to an example embodiment, of an air treatment system, which includes an air treatment appliance and a replaceable cartridge therefor.

With reference to FIGS. 1 through 6, the appliance 100 may further include an electric power plug 125 (e.g., an alternating current power plug) that protrudes directly from the housing 101 to support the plug-in liquid diffusion appliance 100 in a cantilevered manner when installed for use in the electrical wall outlet 10, and for connecting the appliance 100 to a power supply, such as AC main power 112 (FIG. 8). FIGS. 2 and 3 specifically show the appliance 100 plugged into the electrical wall outlet 10 with a full weight of the appliance 100 being supported by the electric power plug 125. As show in FIGS. 1 and 4, the electric power plug 125 may be rigidly coupled to the housing 101 to protrude therefrom with the contacts of the electric power plug 125 being immobile with respect to the housing 101 and the replaceable cartridge 102 when received in the housing 101 for use. In other embodiments, the electric power plug 125 may be rotatably or pivotably coupled to the housing 101 to enable the electric power plug 125 to be deployed from the housing 101 or stored at least partially within the housing 101. In some instances, it is contemplated that the appliance 100 may be used as a freestanding device apart from the electrical wall outlet 10 with the electric power plug 125 in a stored or partially stored configuration. In such instances, the appliance 100 may include on onboard power source (e.g., battery) from which to power the unit and provide other functionality described herein. The onboard power source may be, for example, a rechargeable battery.

As shown in FIG. 4, the housing 101 may include a plurality of housing components 101a, 101b, 101c that combine together to form the housing 101. The housing components 101a, 101b, 101c of the illustrated embodiment include, for example, an upper housing component 101a which includes a cartridge inlet 103 leading to a cartridge-receiving cavity 105 defined by an internal housing framework 101c for receiving the cartridges 102. The upper housing component 101a further supports at least a portion of a control system 128, inclusive of a main printed circuit board (PCB) 129a, which is configured to, among other things, permit adjustment of the timing, flow rate and/or pressure level of the pressurized air generated by a pump assembly 122 that is directed into and passes through an installed cartridge 102 during use. Such adjustments may be provided via wireless user interface controls or the user manipulable controls discussed above. The housing components 101a, 101b, 101c of the illustrated embodiment further include a lower housing component 101b which defines a substantial portion of an external profile of the appliance 100 and which accommodates various functional components of the appliance 100. For example, the lower housing component 101b accommodates and supports the internal housing framework 101c, which in turn supports the pump 122, which is configured to supply a flow of air to the cartridge 102 during operation via a gas supply conduit 124 and stem 126 that is provide at the end of the gas supply conduit 124. The stem 126 is supported within the cartridge receiving cavity 105 of the internal housing framework 101c and is sized and shaped to be insertably received in a bottom end of a loaded cartridge 102.

Figure 6:
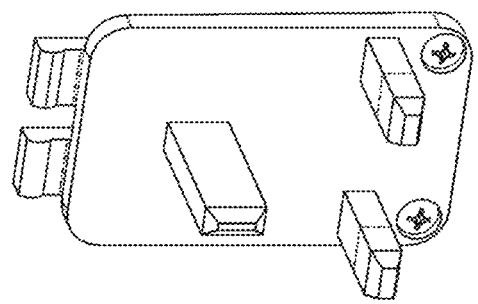
FIG. 6 is a perspective view of other embodiments of power plate assemblies that may be used with the air treatment appliance for adapting the appliance for use with various standard electrical wall outlets around the world.
Figure 6:
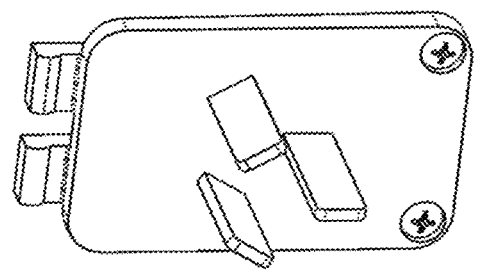
Figure 6:
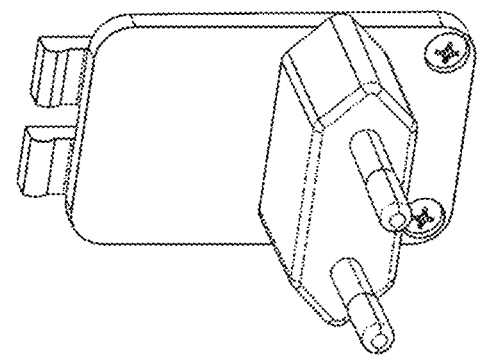
Figure 5:
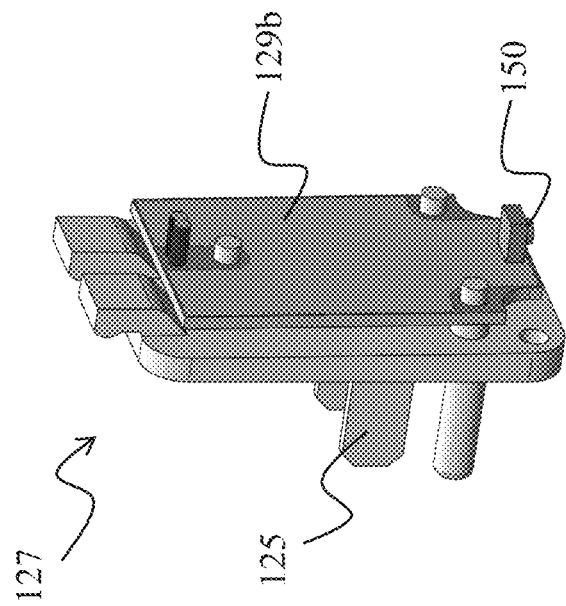
FIG. 5 is a perspective view of a power plate assembly of the air treatment appliance of FIG. 1.

With reference to FIG. 5, the electric power plug 125 may be provided as part of a power plate assembly 127 that may be coupled to the housing 101 by fasteners and/or other well-known fastening structures. The power plate assembly 127 may include a supplemental printed circuit board (PCB) 129b comprising power control electronics and being communicatively coupled to the main printed circuit board (PCB) 129a to form part of the overall control system 128 of the appliance 100. The supplemental printed circuit board (PCB) 129b may also support a lighting element (e.g., LED) 150, which is configured to operate in conjunction with a light guide 151 to form the aforementioned lighting arrangement 109 for emitting light from the appliance 100 in connection with the lighting functionality described herein. Advantageously, the power plate assembly 127 can be provided with different forms of well-known power plug contact arrangements to meet standards in various countries throughout the world. FIG. 6 illustrates, for example, a variety of power plate assemblies with different contact arrangements for different countries around the world. In this manner, the appliance 100 can be readily adapted for worldwide use.

Figure 7:
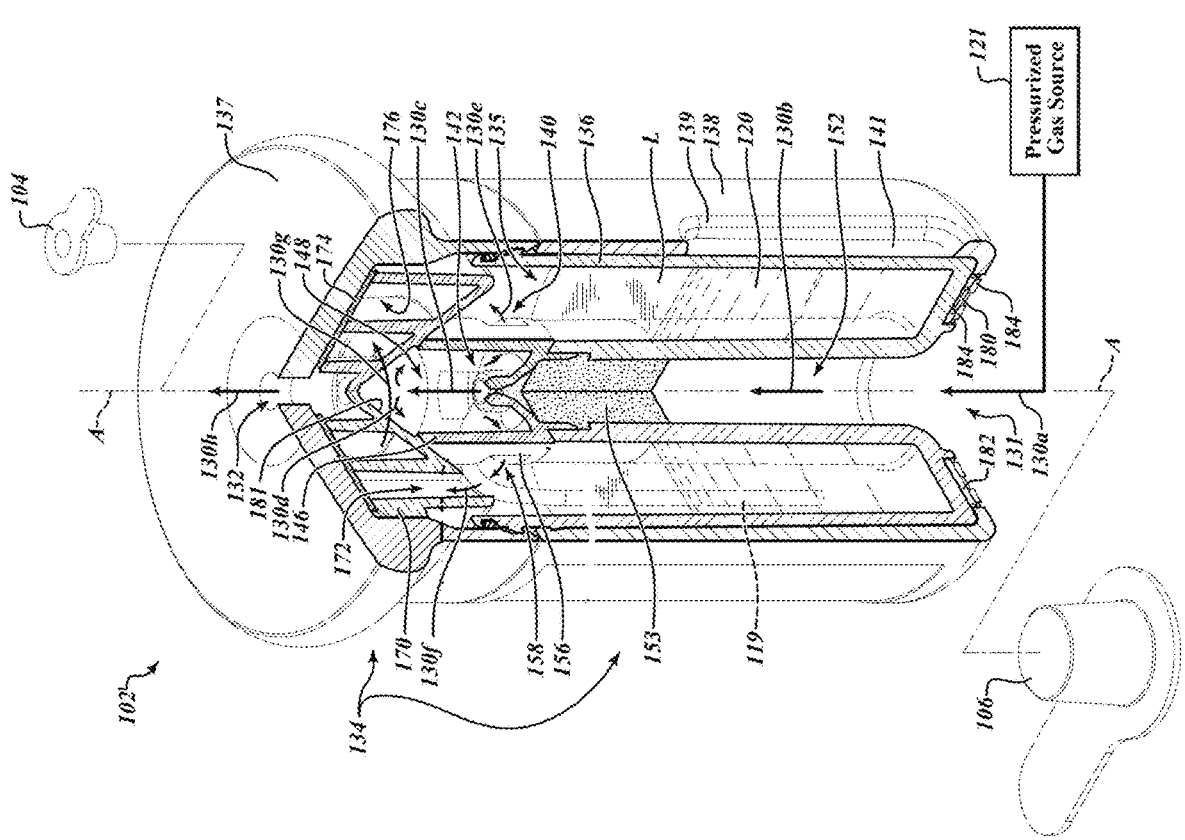
FIG. 7 is an isometric cross-sectional view of an example replaceable cartridge usable with the air treatment appliance of FIG. 1.

FIG. 7 shows further details of a cartridge 102' that is substantially similar to the cartridge 102 illustrated in FIG. 1, and which may be insertably received in the appliance 100 to provide a source of the liquid 120 to be aerosolized. With reference to FIG. 7, the replaceable cartridge 102' may include a cartridge housing 134 comprising a plurality of housing pieces coupled together to define a fluid receptacle having an internal cavity 135, which is partially filled with the liquid 120 to be diffused. For example, in accordance with the example embodiment of the cartridge 102' shown in FIG. 7, the cartridge housing 134 includes an internal housing body 136 defining at least a portion of a receptacle for the liquid 120 to be aerosolized, an upper housing cap 137 including the cartridge outlet 132 through which the aerosolized matter is discharged during use, and an outer casing 138 surrounding at least a lower portion of the internal housing body 136. In some instances, at least some of the housing pieces, for example, the internal housing body 136 and the upper housing cap 137, may be fixedly coupled together to prevent non-destructive disassembly of the cartridge 102', making it effectively tamperproof. This may be desirable to prevent users from refilling and reusing a spent cartridge that may be ineffective or less effective in treating the space due to fouling or build-up of residue within the cartridge 102' from prior use.

As an example, and with reference to FIG. 7, the internal housing body 136 and the upper housing cap 137 may be provided with interlocking structures that snap or otherwise couple together in a manner that prevents non-destructive disassembly of the cartridge housing 134. A seal, such as an o-ring seal or other seal, may be provided between the internal housing body 136 and the upper housing cap 137 near the interlocking structures to provide a liquid tight seal when the cartridge housing 134 is assembled. In this manner, the liquid 120 to be diffused may be prevented from leaking from the cartridge housing 134 at an interface between the internal housing body 136 and the upper housing cap 137. Upon depletion of the liquid 120, the cartridge 102' may be readily removed and replaced with a like cartridge 102' for continued treatment of the environment surrounding the host appliance 100, and the depleted cartridge 102' may be discarded as an intact unit or collected for refurbishment purposes.

With continued reference to FIG. 7, the internal housing body 136 and the outer casing 138 may be provided with interlocking structures that couple together in a manner that prevents disassembly of the outer casing 138 from the internal housing body 136 until a threshold resistive force is overcome, after which the outer casing 138 may be removed from the internal housing body 136. In other instances, the interlocking structures may prevent non-destructive disassembly of the outer casing 138 from the remainder of the cartridge 102' to further assist in making the cartridge 102' tamperproof.

In accordance with the example embodiment of the replaceable cartridge 102' shown in FIG. 7, the internal housing body 136 may be transparent or semi-transparent and the outer casing 138 may be opaque, and the outer casing 138 may be provided with a window 139 through which a level L of the liquid 120 to be aerosolized is viewable through an exposed portion 141 of the transparent or semi-transparent internal housing body 136. Advantageously, the window 139 of the outer casing 138 may have a size and a shape sufficient to observe the liquid level L of the liquid 120 in the internal housing body 136 as the liquid 120 transitions between a full level and an empty level. In this manner, a user can retrieve the cartridge 102' from the appliance 100 as desired and check the level of liquid 120 therein.

Although the cartridge housing 134 of the example cartridge 102' includes a liquid level viewing window 139, in some embodiments, a replaceable cartridge may be provided without such a window 139. In addition, the outer casing 138 may be omitted altogether, such as, for example, as shown in the cartridges 102 of FIG. 1. When provided, the outer casing 138 may have a shape that nests closely with the internal housing body 136. For example, the outer casing 138 and the internal housing body 136 may each have a substantially cylindrical shape concentrically aligned forming a dual layer or dual wall receptacle.

With continued reference to FIG. 7, the internal housing body 136, upper housing cap 137, and outer casing 138 may be fixedly coupled together to define the cartridge housing 134. A cartridge inlet 131 may be provided at a bottom end of the internal housing body 136 to receive a flow of gas (e.g., air) during operation and the cartridge outlet 132 may be provided in the upper housing cap 137 for discharging diffused liquid generated by the cartridge 102' during operation. The cartridge inlet 131 and the cartridge outlet 132 may be aligned along a central axis A defined by the cartridge housing 134. The cartridge housing 134 may be generally rotationally symmetric about the central axis A. For example, as shown in FIG. 7, the cartridge housing 134 may resemble a cylinder or similar receptacle with a mushroom or enlarged top end that is rotationally symmetric about the central axis A. In other instances, the cartridge housing 134 may be asymmetrically shaped and the cartridge inlet 131 and cartridge outlet 132 may not be aligned vertically along a common axis A. Respective caps or plugs 104, 106 may be provided to temporarily close the cartridge inlet 131 and cartridge outlet 132 during storage, transport or the like to prevent fouling or contamination of the cartridge 102' or possible leakage of the liquid 120 contained therein.

Internal components and structures of the cartridge 102' and related functionality will now be described with continued reference to FIG. 7, some of which generally track similar features and functionality disclosed in U.S. Pat. Nos. 9,248,461; 9,162,004; and 10,086,340, which are incorporated by reference in their entireties. According to the illustrated embodiment of the cartridge 102' shown in FIG. 7, the internal components and structures provide, among other things, a flow path through the cartridge 102' from the cartridge inlet 131 to the cartridge outlet 132, as represented by the arrows labeled 130*a*-130*h*. When installed in the host diffusion appliance 100, the cartridge inlet 131 is coupled to a source of pressurized gas 121 (e.g., pump 122 of FIG. 4) such that the gas (e.g., air) may be periodically forced through the cartridge 102' as generally represented by the arrows labeled 130*a*-130*h* to combine with the liquid 120 and to exit as a gas-liquid mixture comprising particularly small liquid particles carried by the gas, referred to generally herein as a diffused liquid or aerosolized matter. Details of the example pump 122 are not shown or described herein to avoid unnecessarily obscuring descriptions of the embodiments; however, it will be appreciated that the pump 122 may be provided in a wide variety of different form factors.

As shown in FIG. 7, the pressurized gas enters the cartridge 102' through the cartridge inlet 131 at a bottom end of the housing 134 and then flows through a diffusion head 140 provided within the housing 134, which includes a venturi device 142 for drawing the retained liquid 120 into the moving gas stream through an intake conduit 119, after which the gas-liquid mixture moves through a cartridge insert 170 before exiting the cartridge 102' through the cartridge outlet 132. More particularly, the pressurized gas enters the cartridge 102' through the cartridge inlet 131 at a bottom end of the housing 134, as represented by the arrow label 130*a*, and then flows upwardly through a gas supply conduit 152 defined by a portion of the internal housing body 136, as represented by the arrow labeled 130*b*. The gas then flows through the venturi device 142 drawing in liquid 120 from a fluid reservoir within the internal housing cavity 135 of the housing 134 via the intake conduit 119 to create a gas-liquid mixture comprising atomized liquid (also referred to herein as diffused liquid or aerosolized matter) that is discharged into an expansion chamber 148 provided by an upper portion 146 of the diffusion head 140, as represented by the arrow labeled 130*c*. The diffused liquid is then directed toward an impact structure or surface 181 located opposite the venturi device 142 wherein at least some of the diffused liquid impacts and collects on the impact structure or surface 181 and is routed back to any remaining liquid 120 in the fluid reservoir to be reintroduced into the gas stream by the venturi device 142. At least some other of the diffused liquid is redirected to flow down around bulkhead portions 156 of the diffusion head 140 and to pass through passageways 158 in the diffusion head 140 leading to a portion of the internal cavity 135 of the cartridge housing 134 above the fluid level L of liquid 120 in the cartridge 102', as represented by the arrows labeled 130*d* and 130*e*. From there, some of the diffused liquid may collect on the exposed interior surfaces of the housing 134 or other internal structures of the cartridge 102', or otherwise precipitate out of the gas and atomized liquid, and rejoin the liquid 120 in the fluid reservoir to be reintroduced into the gas stream by the venturi device 142. Some other of the diffused liquid may be propelled into the cartridge insert 170 via an inlet 172 thereof, as represented by the arrow labeled 130*f*. From the inlet 172 of the insert 170, the diffused liquid proceeds along a tortuous passage (e.g., a spiral passage) through the cartridge insert 170, as represented by the arrow labeled 130*g*, before passing through an outlet zone of the insert 170 and ultimately the cartridge outlet 132 to be discharged from the cartridge 102', as represented by the arrow labeled 130*h*. In making this convoluted journey from the expansion chamber 148 to the cartridge outlet 132, the liquid particle size distribution of the diffused liquid is refined such that only particularly fine particles are successfully discharged from the cartridge 102' with relatively larger particles collecting on one or more surfaces of the internal structures and components of the cartridge 102', or otherwise precipitating out of the gas, for rejoinder with remaining liquid 120 in the liquid reservoir for reintroduction into the gas stream passing through the venturi device 142.

With continued reference to the example embodiment of the replaceable cartridge shown in FIG. 7, it will be appreciated that the cartridge housing 134 and internal components of the cartridge 102' may define a plurality of distinct chambers downstream of the venturi device 142 through which the diffused liquid sequentially travels before being discharged from the cartridge 102' and ultimately into a surrounding environment. More particularly, the upper portion 146 of the diffusion head 140 and a lower portion of the insert 170 may define a primary expansion chamber 148 immediately above the venturi device 142, a secondary chamber may be provided external of the diffusion head 140 and the insert 170 within the internal cavity 135 of the housing 134 above the fluid level L of the liquid 120 to be diffused, and a tertiary chamber may be provided by the tortuous passage 176 of the insert 170. Passageways or apertures 158 in the upper portion 146 of the diffusion head 140 provide fluid communication between the primary expansion chamber 148 and the secondary chamber. The upper portion 146 of the diffusion head 140 also defines a bulkhead or bulkhead portions 156 that impede the diffused liquid generated by the venturi device 142 from exiting the primary expansion chamber 148 other than through the plurality of passageways or apertures 158. The inlet 172 of the insert 170 provides fluid communication between the secondary chamber and the tertiary chamber (i.e., the tortuous passage 176). Although only one inlet 172 and one tortuous passage 176 is shown providing the sole passage for the diffused liquid to exit the cartridge 102', it is appreciated that a plurality of inlets 172 may be provide to enable diffused liquid to enter one or more tortuous passages leading to the outlet 132 of the cartridge 102. A gasket 174 may also be positioned between an upper end of the insert 170 and the upper housing cap 137 with the gasket 174 forming a cover over the tortuous passage 176.

The distinct chambers described above (i.e., the primary expansion chamber, the secondary chamber and the tertiary chamber) may collectively assist in refining the composition of the diffused liquid to include only the finest liquid particles as the diffused liquid moves sequentially through the chambers during operation. For instance, by the time the gas-liquid mixture exits from cartridge 102', there has been some residence time in each of the distinct chambers to permit undesirably large liquid particles or droplets to precipitate out of or otherwise separate from the mixture and be returned to the liquid reservoir within the internal cavity 135 of the housing 134 for later atomization and dispersion. In this manner, the removable cartridge 102' and components thereof may provide a cartridge solution for a liquid diffusion appliance 100, which has an efficient form factor that is particularly effective at treating spaces with diffused liquid having extremely small liquid particles.

With continued reference to FIG. 7, a liquid retention device 153, such as, for example, an open cell foam plug, may be positioned within the gas supply conduit 152 adjacent the venturi device 142 to retain liquid 120 that may pass downward through the venturi device 142 into the gas supply conduit 152. This may occur during shipping as liquid 120 may move through the intake conduit 119 into the venturi device 142 and unwantedly into the gas supply conduit 152. In addition, it may occur when stopping the flow of air through the cartridge 102', which may result in some of the liquid expelled into the expansion chamber 148 settling back down into and passing through the venturi device 142. The liquid retention device 153 may collect liquid 120 that unwantedly passes into the gas supply conduit 152 and retain the liquid 120 therein until the cartridge 102' is used again, at which time the air flowing through the cartridge 102' may clear the liquid 120 from the liquid retention device 153.

With continued reference to FIG. 7, the replaceable cartridge 102' may further comprise an integrated circuit 180 coupled to the cartridge housing 134, the integrated circuit including memory to store cartridge data associated with the replaceable cartridge 102. The cartridge data may include, for example, a type of liquid 120 stored in the cartridge 102', an amount of liquid 120 stored in the cartridge, a cartridge identifier from which to authenticate the cartridge 102', and/or other data. The amount of liquid 120 may be measured directly, indirectly or otherwise estimated by usage history data or other techniques. For example, duration and intensity history data associated with the operation of the host appliance 100 and a particular cartridge 102' may be logged and used to estimate the amount of liquid 120 remaining in the cartridge 102'.

As shown in FIG. 7, the integrated circuit 180 may be embedded in or otherwise coupled to a cartridge printed circuit board (PCB) 182. The cartridge PCB 182 may be coupled to the cartridge housing 134, such as, for example, by adhesive or other joining techniques or devices. According to the example embodiment of the cartridge 102' shown in FIG. 7, the cartridge PCB 182 is located at a bottom end of the cartridge housing 134 and has an annular shape that nests with the bottom end of the cartridge housing 134. The cartridge PCB 182 further comprises an electrical interface 184 in electrical communication with the integrated circuit 180 to enable retrieval of the cartridge data by an external system contacting the electrical interface 184.

To reiterate, the air treatment appliance 100 according to embodiments of the present invention includes a replaceable cartridge 102, 102' containing liquid 120 to be aerosolized and discharged through a cartridge outlet 132, a pump 122 operatively coupled to the replaceable cartridge 102, 102' to supply air to the replaceable cartridge 102, 102' to generate the aerosolized compound from the liquid 120, a control system 128 operatively coupled to the pump 122 for controlling the pump 122 to supply the air to the replaceable cartridge 102, 102' to generate the aerosolized compound and discharge the aerosolized compound from the cartridge outlet 132, and an appliance housing 101 that accommodates the replaceable cartridge 102, 102', the pump 122 and the control system 128 therewithin.

FIG. 8 provides a system diagram, according to one example embodiment, of an air treatment system 200 comprising an air treatment appliance, such as, for example, the example embodiment of the air treatment appliance 100 described above with reference to FIGS. 1 through 4, and a replaceable cartridge installable in the appliance 100 and containing a liquid to be discharged as aerosolized matter, such as the replaceable cartridge 102, 102' shown in FIGS. 1-3 and 7. As can be appreciated from a review of FIG. 8, the appliance 100 may include a control system 128 that is configured to receive one or more control inputs from a physical user interface (e.g., user-manipulable switches or buttons 107, 108) of the appliance 100 and/or an application interface 202, which may be provided via a smartphone or other computing device to control the appliance 100 remotely. The control system 128 is operatively coupled to an air source (e.g., pump 122) for supplying air flow through the cartridge 102 for generating the aerosolized matter from the liquid contained in the cartridge 102 for discharge into the surrounding environment. In some instances, the cartridge 102 may include a cartridge PCB and an associated integrated circuit for storing cartridge information and enabling the transfer of information between the cartridge 102 and the control system 128 to provide enhanced functionality. In some particularly advantageous embodiments, cartridge information may be obtained by the control system 128 and transmitted to a remote device or devices, such as a smartphone, for displaying various indications, alerts or other information to a user of the appliance 100 based at least in part on the information stored by the cartridge 102 and/or control system 128 of the appliance 100. In other instances, the cartridge 102 may lack such a cartridge PCB and associated functionality.

It may be noted that the air treatment appliances 100, replaceable cartridges 102, and components thereof disclosed herein may include operational control via control system 128 for varying the pressure, flow velocity and/or timing of operation of the onboard air source (e.g., pump 122) to provide air flow through the cartridge 102. In addition to using the control system 128 to alter the amount of liquid diffused or aerosolized by the appliance 100 and the corresponding degree of treatment of a space, the control system 128 may be used to provide other functionality. For example, the control system 128 may be used in conjunction with the photodetector 110 and lighting arrangement 109 to provide the lighting functionalities described herein to provide "night light" functionality in addition to scenting or other air treatment functionality.

As another example, the control system 128 may also be in communication with one or more accelerometers or other sensors (e.g., tilt sensor) for detecting motion and/or orientation of the appliance 100 or cartridge 102 and providing enhanced functionality in view of the same, such as disabling operation of the appliance 100 when the appliance 100 or cartridge 102 is not upright or substantially upright.

In connection with the embodiments described herein, it will be also appreciated that various related methods may be provided. For example, one example method implemented by a processor-based electronic liquid diffusion device, such as, for example, the appliance 100 of FIG. 1, may be summarized as including: plugging an electric power plug 125 of the plug-in liquid diffusion appliance 100 into an electrical wall outlet 10, wherein the electric power plug 125 protrudes directly from a housing 100 of the plug-in liquid diffusion appliance 100 and supports the plug-in liquid diffusion appliance 100 in a cantilevered manner; and inserting a replaceable cartridge 102 into the housing through a cartridge port 103 in the housing 101, wherein the replaceable cartridge 102 includes an internal cavity at least partially filled with a liquid 120 to be aerosolized and a venturi device 142 within the internal cavity for generating aerosolized matter from the liquid 120.

The method may further comprise controlling operation of the venturi device 142 using signals generated by a photodetector 110. For example, controlling operation of the venturi device 142 may include initiating operation of the venturi device 142 when a signal generated by the photodetector 110 indicates that the photodetector 110 is located within a light environment (e.g., when a room in which the appliance 100 is installed is illuminated by natural light and/or lighting fixtures of the room itself). Initiating operation of the venturi device 142 may include initiating operation of the venturi device 142 a predetermined amount of time after the signal generated by the photodetector 110 indicates that the photodetector 110 is located within the light environment. The predetermined amount of time may be between 1 minute and 100 minutes, such as 1, 5, 10, 15, 20, 25, 30, 35, 40, 45, 50, 55, 60, 65, 70, 75, 80, 85, 90, 95 or 100 minutes. In one example embodiment, the predetermined amount of time is 30 minutes. As another example, controlling operation of the venturi device 142 may include terminating operation of the venturi device 142 when a signal generated by the photodetector 110 indicates that the photodetector is located within a dark environment (e.g., when a room in which the appliance 100 is installed is not illuminated or only minimally illuminated by natural light and/or lighting fixtures of the room itself). Terminating operation of the venturi device 142 may include terminating operation of the venturi device 142 a predetermined amount of time after the signal generated by the photodetector 110 indicates that the photodetector 110 is located within the dark environment. The predetermined amount of time may be between 1 minute and 100 minutes, such as 1, 5, 10, 15, 20, 25, 30, 35, 40, 45, 50, 55, 60, 65, 70, 75, 80, 85, 90, 95 or 100 minutes. In one example embodiment, the predetermined amount of time is 30 minutes. In this manner, the appliance 100 may operate in a light sensing mode to enable operation of the appliance continuously without further interaction required by a user. The appliance 100 may be maintained in an inactive state when in a dark environment (as determined by the photodetector 110) and, conversely, maintained in an active state when in a light environment (as determined by the photodetector 110)—a so-called "light activation mode". The active state may be characterized by periods in which the appliance 100 is discharging scented (or other air treatment) compounds and periods in which the appliance is not discharging scented (or other air treatment) compounds according to one or more duty cycles or other dispensing programs. In other instances, the appliance 100 may be operated in a manual mode, such as by manually depressing user controls 107 to control the discharging of scented (or other air treatment) compounds, or by interacting with an application interface to control the appliance 100 remotely.

The method may further include calibrating the photodetector 110 to detect light and dark environments. The method may include, for example, receiving a first input from a user via one or more controls mounted to the housing 101 indicating that the photodetector 110 is located within a dark environment having a first amount of ambient light (i.e., a dark environment level); and receiving a second input from the one or more controls mounted to the housing 101 indicating that the photodetector 110 is located within a light environment having a second amount of ambient light greater than the first amount of ambient light (i.e., a light environment level). These amounts or levels of ambient light may be stored in memory for use in controlling or operating the appliance 100. In this manner, a user may program the appliance 100 to recognize a dark environment, and to recognize a light environment. The calibration may be carried out within a specific location or room in which the appliance is to be used such that a user may program the appliance 100 to recognize a dark environment specific to or typical of the location or room in which the appliance is to be used, and to recognize a light environment specific to or typical of the location or room in which the appliance is to be used. In some instances, the calibration may be carried out by a user by pressing a combination of user controls, such as pressing the combination of the "-" and "⌑" controls 107, 108 shown in FIG. 1 for a predetermined amount of time to set a dark point and pressing the combination of the "+" and "⌑" controls 107, 108 shown in FIG. 1 for a predetermined amount of time to set a light point.

Controlling operation of the venturi device 142 may further include initiating operation of the venturi device 142 when a signal generated by the photodetector 110 indicates that the photodetector 110 is located within an environment having an amount of ambient light that is greater than the dark environment level by at least a predetermined amount (e.g., 10%, 15%, 20%, 25%, 30%, 35%, 40%, 45%, 50%, 55%, 60%, 65%, 70%, 75%, 80%, 85%, 95%) of the difference between the dark environment level and the light environment level. For example, operation of the venturi device 142 may be initiated when a signal generated by the photodetector 110 indicates that the photodetector 110 is located within an environment having an amount of ambient light that is greater than the dark environment level by at least 25% of the difference between the dark environment level and the light environment level. This "trigger point" may be adjustable by a user or predetermined and set by the manufacturer.

Similarly, controlling operation of the venturi device 142 may further include terminating operation of the venturi device 142 when a signal generated by the photodetector 110 indicates that the photodetector 110 is located within an environment having an amount of ambient light that is less than the light environment level by at least a predetermined amount (e.g., 10%, 15%, 20%, 25%, 30%, 35%, 40%, 45%, 50%, 55%, 60%, 65%, 70%, 75%, 80%, 85%, 95%) of the difference between the dark environment level and the light environment level. For example, operation of the venturi device 142 may be terminated when a signal generated by the photodetector 110 indicates that the photodetector 110 is located within an environment having an amount of ambient light that is less than the light environment level by at least 75% of the difference between the dark environment level and the light environment level. This "trigger point" likewise may be adjustable by a user or predetermined and set by the manufacturer.

The method may further include halting operation of the plug-in liquid diffusion appliance 100 when one or more accelerometers or other sensors, e.g., a tilt sensor, which is/are configured to measure an orientation of the plug-in liquid diffusion appliance 100, detects that the plug-in liquid diffusion appliance 100 is not upright or substantially upright. Such functionality may be particularly advantageous in embodiments wherein the electric power plug 125 is rotatably or pivotally coupled to the housing 101 in a deployable manner and can therefore vary in angular orientation relative to the housing 100, and/or in embodiments wherein the appliance 100 may be configured to be used in a tabletop or standalone configuration. In this manner, the appliance 100 may be disabled when the appliance 100 is not upright or substantially upright.

Other methods of operating or controlling the plug-in liquid diffusion appliance 100, or aspects thereof, will be appreciated by those of ordinary skill in the relevant art upon a detailed review of the present disclosure.

Again, although certain specific details are set forth in order to provide a thorough understanding of various disclosed embodiments, one skilled in the relevant art will recognize that embodiments may be practiced without one or more of these specific details. Moreover, aspects and features of the various embodiments described above can be combined to provide further embodiments. All of the U.S. patents referred to in this specification are incorporated herein by reference, in their entirety. Aspects of the embodiments can be modified, if necessary to employ features, structures, functionality or concepts of the various patents to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A plug-in liquid diffusion appliance comprising:
   a replaceable cartridge including:
   an internal cavity at least partially filled with a liquid to be aerosolized; and
   a venturi within the internal cavity for generating aerosolized matter from the liquid;
   a housing including a cartridge port through which to receive the replaceable cartridge;
   an electric power plug that protrudes directly from the housing to support the plug-in liquid diffusion appliance in a cantilevered manner when installed for use in an electrical wall outlet; and
- a tilt sensor configured to measure an orientation of the plug-in liquid diffusion appliance.

2. The plug-in liquid diffusion appliance of claim 1, wherein the electric power plug is an alternating current power plug.

3. The plug-in liquid diffusion appliance of claim 1, wherein the electric power plug is rigidly coupled to the housing.

4. The plug-in liquid diffusion appliance of claim 1, wherein contacts of the electric power plug are immobile with respect to the housing.

5. The plug-in liquid diffusion appliance of claim 1, wherein contacts of the electric power plug are immobile with respect to the replaceable cartridge when the replaceable cartridge is received within the housing.

6. The plug-in liquid diffusion appliance of claim 1, wherein, when the electric power plug is plugged into the electrical wall outlet, a full weight of the plug-in liquid diffusion appliance is supported by the electric power plug.

7. The plug-in liquid diffusion appliance of claim 1, further comprising:
a photodetector mounted to the housing, wherein the plug-in liquid diffusion appliance is configured to be controlled using signals generated by the photodetector.

8. The plug-in liquid diffusion appliance of claim 7, wherein the plug-in liquid diffusion appliance is configured to control operation of the venturi using signals generated by the photodetector.

9. The plug-in liquid diffusion appliance of claim 7, wherein the photodetector is mounted to a top of the housing.

10. The plug-in liquid diffusion appliance of claim 7, wherein the photodetector is mounted to an upward-facing portion of the housing.

11. The plug-in liquid diffusion appliance of claim 7, further comprising:
a light source mounted to the housing.

12. The plug-in liquid diffusion appliance of claim 11, wherein the plug-in liquid diffusion appliance is configured to control the light source using signals generated by the photodetector.

13. The plug-in liquid diffusion appliance of claim 11, wherein the light source is mounted to a bottom of the housing.

14. The plug-in liquid diffusion appliance of claim 7, further comprising:
one or more controls mounted to the housing, the one or more controls configured to receive a first input from a user and generate a first signal indicating that the photodetector is located within a dark environment, and to receive a second input from the user and generate a second signal indicating that the photodetector is located within a light environment.

15. A method of operating a plug-in liquid diffusion appliance comprising:
plugging an electric power plug of the plug-in liquid diffusion appliance into an electrical wall outlet, wherein the electric power plug protrudes directly from a housing of the plug-in liquid diffusion appliance and supports the plug-in liquid diffusion appliance in a cantilevered manner, and wherein the plug-in liquid diffusion appliance includes a tilt sensor configured to measure an orientation of the plug-in liquid diffusion appliance;
inserting a replaceable cartridge into the housing through a cartridge port in the housing, wherein the replaceable cartridge includes an internal cavity at least partially filled with a liquid to be aerosolized and a venturi within the internal cavity for generating aerosolized matter from the liquid; and
halting operation of the plug-in liquid diffusion appliance when the tilt sensor detects that the plug-in liquid diffusion appliance is not upright.

16. A method of operating a plug-in liquid diffusion appliance comprising:
plugging an electric power plug of the plug-in liquid diffusion appliance into an electrical wall outlet, wherein the electric power plug protrudes directly from a housing of the plug-in liquid diffusion appliance and supports the plug-in liquid diffusion appliance in a cantilevered manner, and wherein the plug-in liquid diffusion appliance includes a photodetector mounted to the housing;
inserting a replaceable cartridge into the housing through a cartridge port in the housing, wherein the replaceable cartridge includes an internal cavity at least partially filled with a liquid to be aerosolized and a venturi within the internal cavity for generating aerosolized matter from the liquid;
receiving a first input from a user indicating that the photodetector is located within a dark environment having a first amount of ambient light to calibrate the plug-in liquid diffusion appliance to recognize the dark environment;
receiving a second input from the user indicating that the photodetector is located within a light environment having a second amount of ambient light greater than the first amount of ambient light to calibrate the plug-in liquid diffusion appliance to recognize the light environment; and
controlling operation of the venturi using signals generated by the photodetector, including initiating operation of the venturi when a signal generated by the photodetector indicates that the photodetector is located within an environment having a third amount of ambient light that is greater than the first amount of ambient light by a predetermined percentage of the difference between the first amount of ambient light and the second amount of ambient light.

17. The method of claim 16, wherein controlling operation of the venturi includes initiating operation of the venturi when a signal generated by the photodetector indicates that the photodetector is located within the light environment.

18. The method of claim 16, wherein the predetermined percentage of the difference between the first amount of ambient light and the second amount of ambient light is 25 percent.

19. The method of claim 16, wherein controlling operation of the venturi includes terminating operation of the venturi when a signal generated by the photodetector indicates that the photodetector is located within the dark environment.

20. A method of operating a plug-in liquid diffusion appliance comprising:
plugging an electric power plug of the plug-in liquid diffusion appliance into an electrical wall outlet, wherein the electric power plug protrudes directly from a housing of the plug-in liquid diffusion appliance and supports the plug-in liquid diffusion appliance in a cantilevered manner, and wherein the plug-in liquid diffusion appliance includes a photodetector mounted to the housing;
inserting a replaceable cartridge into the housing through a cartridge port in the housing, wherein the replaceable cartridge includes an internal cavity at least partially filled with a liquid to be aerosolized and a venturi within the internal cavity for generating aerosolized matter from the liquid;
receiving a first input from a user indicating that the photodetector is located within a dark environment having a first amount of ambient light to calibrate the plug-in liquid diffusion appliance to recognize the dark environment;
receiving a second input from the user indicating that the photodetector is located within a light environment having a second amount of ambient light greater than the first amount of ambient light to calibrate the plug-in liquid diffusion appliance to recognize the light environment; and
controlling operation of the venturi using signals generated by the photodetector, including terminating operation of the venturi when a signal generated by the photodetector indicates that the photodetector is located within an environment having a third amount of ambient light that is less than the second amount of ambient light by a predetermined percentage of the difference between the first amount of ambient light and the second amount of ambient light.

21. The method of claim 20, wherein the predetermined percentage of the difference between the first amount of ambient light and the second amount of ambient light is 75 percent.

22. A method of operating a plug-in liquid diffusion appliance comprising:
  plugging an electric power plug of the plug-in liquid diffusion appliance into an electrical wall outlet, wherein the electric power plug protrudes directly from a housing of the plug-in liquid diffusion appliance and supports the plug-in liquid diffusion appliance in a cantilevered manner, and wherein the plug-in liquid diffusion appliance includes a photodetector mounted to the housing;
  inserting a replaceable cartridge into the housing through a cartridge port in the housing, wherein the replaceable cartridge includes an internal cavity at least partially filled with a liquid to be aerosolized and a venturi within the internal cavity for generating aerosolized matter from the liquid;
  receiving a first input from a user indicating that the photodetector is located within a dark environment having a first amount of ambient light to calibrate the plug-in liquid diffusion appliance to recognize the dark environment;
  receiving a second input from the user indicating that the photodetector is located within a light environment having a second amount of ambient light greater than the first amount of ambient light to calibrate the plug-in liquid diffusion appliance to recognize the light environment; and
  controlling operation of the venturi using signals generated by the photodetector, including terminating operation of the venturi when a signal generated by the photodetector indicates that the photodetector is located within the dark environment, and wherein the terminating operation of the venturi includes terminating operation of the venturi a predetermined amount of time after the signal generated by the photodetector indicates that the photodetector is located within the dark environment.

23. The method of claim 22, wherein the predetermined amount of time is between one minute and one hundred minutes.

24. The method of claim 23, wherein the predetermined amount of time is thirty minutes.

* * * * *